United States Patent
Ohtake et al.

(10) Patent No.: US 8,128,565 B2
(45) Date of Patent: Mar. 6, 2012

(54) HEAT REDUCING ULTRASOUND DIAGNOSTIC APPARATUS

(75) Inventors: Akifumi Ohtake, Mitaka (JP); Katsufumi Motokawa, Mitaka (JP)

(73) Assignee: Aloka Co., Ltd., Tokyo (JP)

( * ) Notice: Subject to any disclaimer, the term of this patent is extended or adjusted under 35 U.S.C. 154(b) by 878 days.

(21) Appl. No.: 11/347,968

(22) Filed: Feb. 6, 2006

(65) Prior Publication Data

US 2006/0241464 A1    Oct. 26, 2006

(30) Foreign Application Priority Data

Feb. 18, 2005    (JP) ................ 2005-041604

(51) Int. Cl.
*A61B 8/00* (2006.01)
*A61B 8/14* (2006.01)

(52) U.S. Cl. ......... 600/441; 600/459; 600/437; 600/457
(58) Field of Classification Search ............ 600/447
See application file for complete search history.

(56) References Cited

U.S. PATENT DOCUMENTS

| | | | |
|---|---|---|---|
| 4,265,126 A | | 5/1981 | Papadofrangakis et al. |
| 5,175,709 A * | | 12/1992 | Slayton et al. ............ 367/90 |
| 5,261,408 A | | 11/1993 | Maslak et al. |
| 6,669,638 B1 * | | 12/2003 | Miller et al. ............ 600/438 |
| 6,682,482 B1 | | 1/2004 | Krishnan |
| 6,814,701 B1 | | 11/2004 | Tamura |
| 7,399,279 B2 * | | 7/2008 | Abend et al. ............ 600/450 |
| 2002/0035328 A1 * | | 3/2002 | Roundhill et al. ............ 600/443 |
| 2004/0116810 A1 * | | 6/2004 | Olstad ............ 600/443 |
| 2004/0254465 A1 * | | 12/2004 | Sano et al. ............ 600/443 |
| 2004/0267127 A1 * | | 12/2004 | Abend et al. ............ 600/450 |
| 2007/0167771 A1 * | | 7/2007 | Olstad ............ 600/437 |
| 2008/0027323 A1 * | | 1/2008 | Freiburger ............ 600/453 |

FOREIGN PATENT DOCUMENTS

| | | |
|---|---|---|
| EP | 0 335 578 | 10/1989 |
| JP | 62-22637 | 1/1987 |
| JP | 10-75954 | 3/1998 |
| JP | 2004-57460 | 2/2004 |
| JP | 2004-159832 | 6/2004 |
| WO | WO 96/04588 | 2/1996 |

* cited by examiner

*Primary Examiner* — Unsu Jung
*Assistant Examiner* — Angela M Hoffa
(74) *Attorney, Agent, or Firm* — DLA Piper LLP (US)

(57) ABSTRACT

An ultrasound diagnostic apparatus having a continuous wave Doppler mode. A line switching section is provided between an array transducer and a unit which has a CW transmission section and a CW reception section, for changing a transmitting and receiving aperture pattern. When a first transmitting and receiving aperture pattern is set on the array transducer, a first aperture functions as a transmitting aperture and a second aperture functions as a receiving aperture. When a second transmitting and receiving aperture pattern is set on the array transducer, the second aperture functions as a transmitting aperture and a first aperture functions as a receiving aperture. The patterns are switched whenever predetermined amount of time has elapsed after a prescribed event such as a pattern change, resumption of continuous wave reception, and so on. As such, localized heat generation or deterioration on the array transducer can be prevented.

9 Claims, 8 Drawing Sheets

HEAT REDUCING ULTRASOUND DIAGNOSTIC APPARATUS

BACKGROUND OF THE INVENTION

1. Field of the Invention

The present invention relates to an ultrasound diagnostic apparatus, and more particularly to an ultrasound diagnostic apparatus having a continuous wave Doppler mode.

2. Description of Related Art

In a continuous wave Doppler mode, ultrasound (a continuous wave) is transmitted from an ultrasound probe into a living body, and a reflected wave (a continuous wave) subject to the Doppler effect due to the flowing of blood within the living body is received by the ultrasound probe. By applying frequency analysis to Doppler frequency components of a received signal, a Doppler waveform can be formed, as described in Japanese Patent Laid-Open Publication No. Sho 62-22637 (Reference 1).

Conventionally, in the continuous wave Doppler mode, a transmitting aperture and a receiving aperture are fixedly set on an array transducer provided in a probe, as described in Japanese Patent Laid-Open Publication No. 2004-159832 (Reference 2). With this structure, only a specific portion (i.e. the transmitting aperture) on the array transducer continuously generates heat, leading to a temperature gradient on a transmitting and receiving surface of the probe. For safety considerations, it is necessary that the temperature of the transmitting and receiving surface of the probe be maintained below a predetermined temperature. Accordingly, conventionally, when the temperature of the transmitting and receiving surface of the probe reaches the allowable limit, the power of the ultrasound to be transmitted is decreased. Such a decrease in the power of the ultrasound, however, reduces the sensitivity of the apparatus. Also, continuous use of a specific section of the array transducer as the transmitting aperture accelerates deterioration of that section, which reduces the operating life of the probe. Japanese Patent Laid-Open Publication No. 2004-057460 (Reference 3) describes setting of a transmitting aperture and a receiving aperture on an array transducer arranged two-dimensionally. In Reference 3, however, these apertures are arranged in a fixed manner.

Japanese Patent Laid-Open Publication No. Hei 10-75954 (Reference 4) discloses a structure in which the ratio of the size of a transmitting aperture and the size of a receiving aperture on an array transducer is variable in accordance with, the position of a measuring target (particularly, in accordance with the beam direction). Further, Reference 4 describes that when the measuring target is located toward the right with respect to the front of the probe, a transmitting aperture is set on the right side of the array transducer and a receiving aperture is set on the left side of the array transducer, whereas, when the measuring target is located toward the left with respect to the front of the probe, the transmitting aperture is set on the left side of the array transducer and the receiving aperture is set on the right side of the array transducer. In the structure described in Reference 4, however, if the position of the measuring target is unchanged (more specifically, unless the measuring target is changed toward right or left beyond the front position), the position of the transmitting aperture on the array transducer also remains unchanged. In addition, Reference 4 includes no description concerning countermeasures against heat generation or deterioration of the array transducer.

U.S. Pat. No. 6,669,638 (Reference 5) discloses a system for controlling the temperature of a transducer. While Reference 5 describes that a transmitting aperture and a receiving aperture are changed in accordance with the depth of the area being imaged, it does not describe that a transmitting aperture and a receiving aperture are changed in accordance with the temperature or that aperture patterns are switched.

SUMMARY OF THE INVENTION

The present invention advantageously solves or alleviates problems resulting from setting of a transmitting aperture in a fixed manner on an array transducer in a continuous wave Doppler mode.

The present invention further advantageously prevents a heat generating portion from being set in a fixed manner on an array transducer in a continuous wave Doppler mode.

The present invention still further advantageously ensures equal wear of a plurality of transducer elements forming an array transducer in continuous wave Doppler mode.

In accordance with one aspect, an ultrasound diagnostic apparatus according to the present invention comprises an array transducer including a plurality of transducer elements, a transmission section for supplying a plurality of continuous transmitting signals to a plurality of transducer elements forming a transmitting aperture which is set on the array transducer in continuous wave Doppler mode, a reception section for processing a plurality of continuous receiving signals supplied from a plurality of transducer elements forming a receiving aperture which is set on the array transducer in the continuous wave Doppler mode, and a control section for sequentially changing a transmitting and receiving aperture pattern set on the array transducer to thereby sequentially change a position of the transmitting aperture which is set on the array transducer in the continuous wave Doppler mode.

With the above structure, the control section changes or switches the transmitting and receiving aperture pattern set on the array transducer. Consequently, the position of the transmitting aperture on the array transducer is sequentially changed with respect to time (i.e. the heat generating portion is set in a dispersed manner), so that a problem that only a specific section of the array transducer continuously generates heat can be prevented, along with the otherwise resulting rise in temperature. Further, the overall wear of a plurality of transducer elements can be equalized, thereby prolonging the overall life of the instrument.

Preferably, alternate selection between two transmitting and receiving aperture patterns are performed. Alternatively, selection among three or more transmitting and receiving aperture patterns may be performed in a predetermined order, or randomly. It may be desirable that two transmitting apertures do not overlap each other either before or after the pattern change. In any event, by performing selection among a plurality of transmitting and receiving aperture patterns in rotation, the transmitting aperture on the array transducer can be moved sequentially to thereby solve or alleviate the above problems. A typical transmitting and receiving aperture pattern includes a transmitting aperture having a block shape, a receiving aperture having a block shape, and one or a plurality of inoperable transducer elements which are set between these apertures. It is desirable that the transmitting aperture and the receiving aperture are formed symmetrically with respect to the center of the array transducer. The transmitting aperture and the receiving aperture, however, may have different sizes or may not be symmetrical.

It is also possible, by applying known beam steering technology and electronic focusing technology, to steer a transmitting beam formed by the transmitting aperture and a receiving beam formed by the receiving aperture in desired directions, and also to set foci of the transmitting and receiving beams to a desired depth. Each of the transmitting and receiving beams is set such that both beams pass through a measurement target (e.g. a blood vessel or valve of heart), and the focus of each beam is set in accordance with the depth of the target. While the array transducer is desirably a 1D array transducer, other configurations, such as a 2D array transducer, may be employed.

Preferably, the control section resets the transmitting and receiving aperture pattern set on the array transducer whenever a certain amount of time has elapsed since the previous pattern change. Because this structure provides time control of the transmitting and receiving aperture pattern, a situation in which a specific pattern is continuously selected for a long time period, i.e. a situation in which a single transmitting aperture is used for a long time, can be prevented. The elapsed time can be measured using a timer or the like. While the switching time is preferably set in units of seconds or minutes, it can be freely set as may be appropriate to the use conditions.

Preferably, the switching time is variable in accordance with a transmission condition. For example, it may be desirable that a switching interval is set based on a transmission condition (i.e. a condition associated with heat generation) such as a transmitting power, a transmitting voltage, and so on. The switching interval may be reset by a user.

Preferably, the control section changes the transmitting and receiving aperture pattern set on the array transducer while transmission and reception of a continuous wave is being performed with respect to a specific measuring target. With this structure, even when ultrasound diagnosis with respect to the specific measuring target is prolonged, the transmitting and receiving aperture pattern is automatically changed, so that a localized temperature increase on the array transducer can be prevented. When wave transmission and reception stops instantaneously at the time of a pattern change, it is preferable to correct a waveform image so as to prevent such an effect from appearing on the displayed waveform image. Here, when a display mode in which a waveform image spreads in the direction of a time axis and is periodically refreshed is selected, it is desirable to change the transmitting and receiving aperture pattern in synchronism with this refresh timing.

Preferably, the transmitting aperture before the change of the transmitting and receiving aperture pattern and the transmitting aperture after the change of the transmitting and receiving aperture pattern do not overlap with each other, thereby making it possible to prevent continuous use of any transducer element for transmission.

Preferably, the control section changes the transmitting and receiving aperture pattern set on the array transducer when reception and transmission of a continuous wave is resumed. The transmitting and receiving aperture pattern is changed when the continuous wave Doppler mode is selected again or when a measuring portion is newly set, for example. The changing method based on the time control as described above may be used together with such a changing method based on a measuring operation.

Preferably, the control section selectively sets the transmitting and receiving aperture pattern among a plurality of transmitting and receiving aperture patterns including a first transmitting and receiving aperture pattern and a second transmitting and receiving aperture pattern set on the array transducer, and the first transmitting and receiving aperture pattern has a transmitting aperture set on one side of the array transducer and a receiving aperture set on the other side of the array transducer and the second transmitting and receiving aperture pattern has a receiving aperture set on the one side of the array transducer and a transmitting aperture set on the other side of the array transducer. Preferably, the control section selects the first transmitting and receiving aperture pattern and the second transmitting and receiving aperture pattern alternately.

Further preferably, the transmitting aperture of the first transmitting and receiving aperture pattern and the receiving aperture of the second transmitting and receiving aperture pattern have the same size and are set at the same position, and the receiving aperture of the first transmitting and receiving aperture pattern and the transmitting aperture of the second transmitting and receiving aperture pattern have the same size and are set at the same position. With this structure, because the beam angle condition is unchanged, the need for angle correction before and after the pattern change can be eliminated, as will be described below. More specifically, it is possible to maintain the rate range and the base line of Doppler waveform before and after the pattern change. Here, the rate correction relying on an angle formed by the blood flow direction and the beam direction, which has been performed in conventional apparatuses, may be performed independently of the angle correction, as described above.

Preferably, the apparatus further includes a line switching section which is provided between the array transducer, and the transmission section and the reception section, and the control section controls the line switching section to thereby sequentially change the transmitting and receiving aperture pattern set on the array transducer.

Preferably, the ultrasound diagnostic apparatus includes an ultrasound probe having the array transducer and an apparatus body to which the ultrasound probe is connected, and the line switching section is provided in the ultrasound probe. The line switching section may be contained within a probe connector or a probe head. Preferably, the ultrasound diagnostic apparatus includes an ultrasound probe having the array transducer and an apparatus body to which the ultrasound probe is connected, and the line switching section is provided in the apparatus body.

Preferably, the transmission section and the reception section are dedicated circuits used exclusively in connection with the continuous wave Doppler mode, and the line switching section includes means for selectively connecting a plurality of signal lines connected to a plurality of transducer elements within a first region of the array transducer to the transmission section or the reception section and means for selectively connecting a plurality of signal lines connected to a plurality of transducer elements within a second region of the array transducer to the transmission section or the reception section, and the control section, when the first transmitting and receiving aperture pattern is selected, connects the plurality of signal lines connected to the plurality of transducer elements within the first region to the transmission section and connects the plurality of signal lines connected to the plurality of transducer elements within the second region to the reception section, and when the second transmitting and receiving aperture pattern is selected, connects the plurality of signal lines connected to the plurality of transducer elements within the first region to the reception section and connects the plurality of signal lines connected to the plurality of transducer elements within the second region to the transmission section.

Preferably, the apparatus further includes image forming means for forming a waveform image based on a receiving signal having been processed which is output from the reception section and a display section for displaying the waveform image. Preferably, the apparatus further includes an image correction section for correcting the waveform image so as to prevent an effect caused by the change of the transmitting and receiving aperture pattern from appearing on the waveform image.

Here, the waveform image to be corrected may be a Doppler waveform itself, a trace waveform (a trace line) formed by tracing the Doppler waveform, or both. Preferably, the image correction section performs a correction process so as to eliminate discontinuity of the waveform image generated at the time of change of the transmitting and receiving aperture pattern.

As already described above, the above-mentioned Reference 4 describes a structure in which a transmitting aperture and a receiving aperture are exchanged depending on whether the beam direction (the position of a measuring target) is located toward the right or the left with respect to the reference (the 0 degree angle) in front of the array transducer. With this structure, however, if the beam direction is maintained on a specific side, the position of the transmitting aperture remains unchanged. According to an embodiment of the present invention as will be described below, however, the transmitting aperture and the receiving aperture are varied in consideration of dispersion of heat generation and dispersion of degradation, irrespective of the beam direction. The timing for the change may be based on elapsed time, a specific event (such as resumption of transmission and reception, reset of a measuring target, refresh of display, and so on), or any combination thereof.

BRIEF DESCRIPTION OF THE DRAWINGS

Preferred embodiments of the present invention will be described in detail based on the following figures, wherein.

DETAILED DESCRIPTION OF PREFERRED EMBODIMENTS

Preferred embodiments of the present invention will be described in detail with reference to the accompanying drawings.

Figure 1:
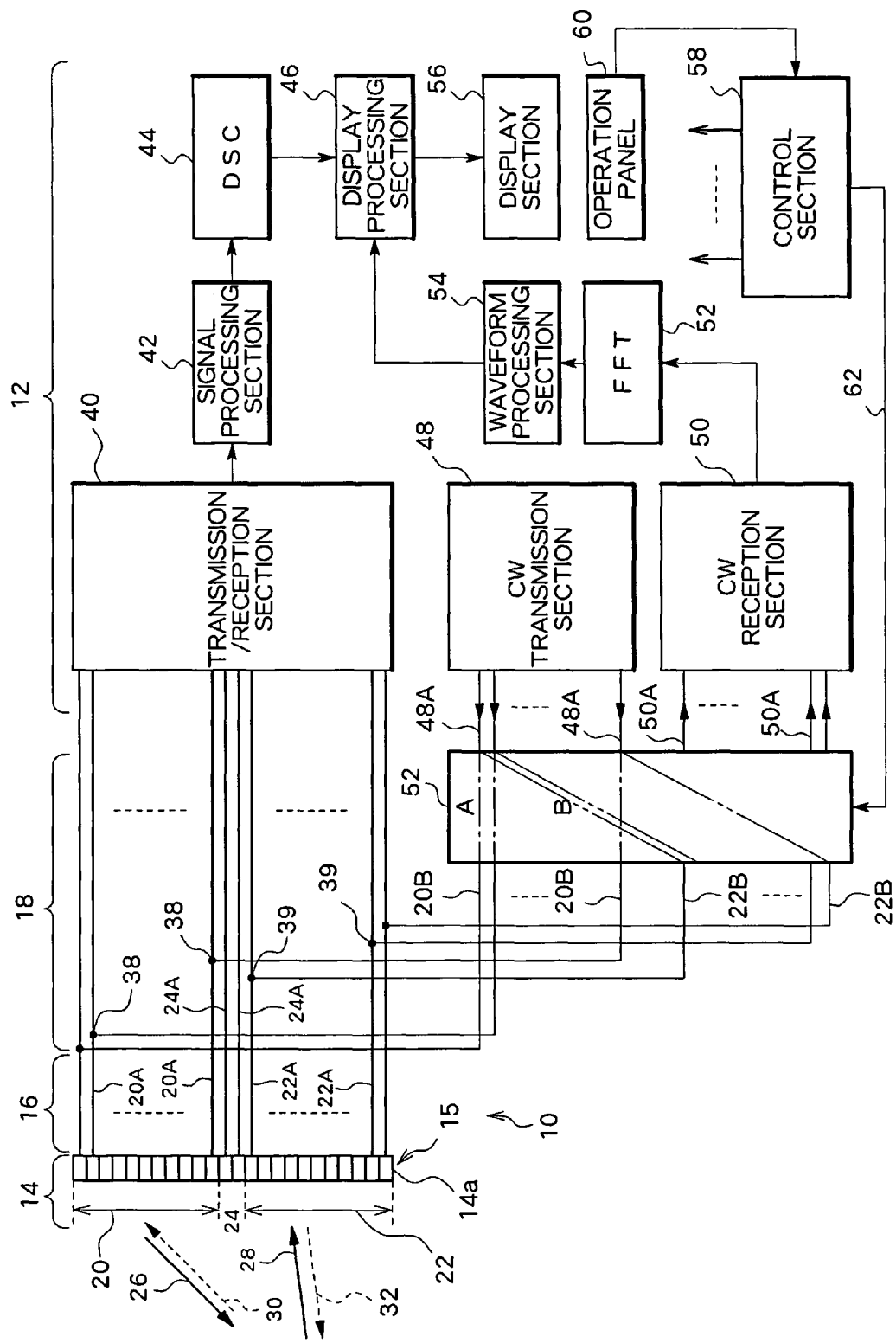
FIG. 1 is a block diagram showing an ultrasound diagnostic apparatus according to a preferred embodiment of the present invention.

FIG. 1 is a block diagram showing a structure of an ultrasound diagnostic apparatus according to an embodiment of the present invention. This ultrasound diagnostic apparatus transmits and receives ultrasound with respect to a living body, obtains a receiving signal, and forms an ultrasound image based on the receiving signal. This ultrasound diagnostic apparatus provides a plurality of operational modes including a continuous wave Doppler mode (CW mode). In the following, the structure of the ultrasound diagnostic apparatus will be described mainly with regard to the continuous wave Doppler mode.

Referring to FIG. 1, the ultrasound diagnostic apparatus includes an apparatus body 12 and a probe 10. In the example shown in FIG. 1, the probe 10 is composed of a probe head 14, a probe cable 16, and a probe connector 18. The probe connector 18 is detachably connected to a connector provided in the apparatus body 12. In the example shown in FIG. 1, the probe connector 18 includes a line switching section 52. The line switching section 52, however, may be provided within the apparatus body 12 or within the probe head 14, as will be described below. Normally, a plurality of probes can be simultaneously connected to the ultrasound diagnostic apparatus. In this case, the plurality of probes are connected, via a probe selector (a switching circuit), to a circuit which generates a transmitting signal and a circuit which processes a receiving signal. Such a probe selector is not shown in FIG. 1. A separate CW line switching section as will be described below may be provided independently of the probe selector, or the probe selector may be configured to provide the function of a CW line switching section.

An array transducer 15 is provided within the probe head 14. In the example shown in FIG. 1, the array transducer 15 is composed of a plurality of transducer elements 14a arranged in a line. These transducer elements 14a may be arranged in an arc shape. Further, a so-called 2D array transducer may be provided within the probe head 14. In the continuous wave Doppler mode, a first aperture 20 and a second aperture 22 are set on the array transducer 15. A gap region 24 is set between the first and second apertures 20 and 22 so as to prevent acoustic crosstalk. In the example shown in FIG. 1, the first aperture 20 and the second aperture 22 are set symmetrically with respect to the center of the array transducer 15 such that they have the same size. Each of these apertures 20 and 22 is formed of about 100 transducer elements, for example. The gap region 24 is formed by approximately several to ten inoperable transducer elements. When a first transmitting and receiving aperture pattern is selected, the first aperture 20 functions as a transmitting aperture and the second aperture 22 functions as a receiving aperture. In other words, a transmitting beam 26 is formed, and a receiving beam 28 is formed. When, on the other hand, a second transmitting and receiving aperture pattern is selected, the second aperture 22 functions as a transmitting aperture and the first aperture 20 functions as a receiving aperture. In this structure, a transmitting beam 32 is formed, and then a receiving beam 30 is formed. As such, the positions of the transmitting aperture and the receiving aperture are interchanged when the pattern is switched. The sizes of the transmitting aperture and of the receiving aperture may be varied in accordance with a target position (the depth and the direction of the target).

The transmitting beam 26, 32 and the receiving beam 28, 30 are formed using electronic beam steering technology and electronic focusing technology. The angle of deflection of each beam is set such that both beams cross each other at the target position which is set within the living body. As is known, in the continuous wave Doppler mode, the transmitting beam is continuously formed, as is the receiving beam.

In the above example, a change of the transmitting and receiving aperture pattern in the continuous wave Doppler mode has been described. In other display modes, such as a B mode, the transmitting and receiving apertures are formed in accordance with an electronic scanning method, such as an electronic sector scan, electronic linear scan, or the like.

One end of each of a plurality of signal lines 20A is connected to each of the plurality of transducer elements forming the first aperture 20, with the other end of each signal line 20A being connected to a transmission/reception section 40. Similarly, one end of each of a plurality of signal lines 22A is connected to each of the plurality of transducer elements forming the second aperture 22, with the other end of each signal line 22A being connected to the transmission/reception section 40. One end of each of a plurality of signal lines 24A is connected to each of the plurality of transducer elements forming the gap region 24, with the other end of each signal line 24A being connected to the transmission/reception section 40.

As shown in FIG. 1, branch points 38 are set in the plurality of signal lines 20A corresponding to the first aperture 20, and a plurality of signal lines 20B extend from these branch points 38. In a similar manner, branch points 39 are set in the plurality of signal lines 22A corresponding to the second aperture 22, and a plurality of signal lines 22B extend from these branch points 39. Such a branch point is not set on the plurality of signal lines 24A corresponding to the gap region 24.

In the example shown in FIG. 1, the plurality of branch points 38 and 39 are provided within the probe connector 18. Alternatively, these branch points 38 and 39 may be provided within the probe head 14 or within the apparatus body 12. When the plurality of branch points 38 and 39 are provided within the probe head 14, however, the number of signal lines forming the probe cable 16 increases. It is therefore preferable to provide these branch points 38 and 39 within the probe connector 18. Further, if these branch points 38 and 39 and the line switching section 52 are provided within the apparatus body 12, the number of connecting lines between the ultrasound probe 10 and the apparatus body 12 can be advantageously reduced. On the other hand, if the branch points 38 and 39 and the line switching section 52 are provided within the probe connector 18, the advantage that the transmitting and receiving aperture pattern can be switched in a simple manner with the main structure of the conventional ultrasound diagnostic apparatus being maintained (although the structure for line switching control need to be added) can be achieved.

The transmission/reception section 40, in the B mode or the like, supplies a plurality of transmitting signals to the plurality of transducer elements 14a and performs a phase alignment and summation process with respect to a plurality of receiving signals output from the plurality of transducer elements 14a. Namely, the transmission/reception section 40 functions as both a transmitting beam former and a receiving beam former. In the B mode, an ultrasound pulse is transmitted within a living body. In the continuous wave Doppler mode, on the other hand, ultrasound serving as a continuous wave is transmitted within a living body.

A signal processing section 42 performs necessary signal processing, such as detection and logarithm compression, on the receiving signal subjected to the phase alignment and summation process as output from the transmission/reception section 40. The processed receiving signal (echo data) is input to a digital scan converter (DSC) 44, which performs coordinate transformation and interpolation based on the input echo data. Thus, a B-mode image is formed as a two-dimensional tomographic image, and the image data is then output to a display processing section 46. Naturally, in addition to the structure shown in FIG. 1, a structure for forming a two-dimensional blood flow image, a structure for forming an M mode image, a structure for forming a Doppler waveform in pulse Doppler mode, and so on may be added. Alternatively, a structure for forming a three-dimensional image may also be added.

The line switching section 52 is a circuit which changes the transmitting and receiving aperture pattern in accordance with a control signal 62 output from a control section 58. More specifically, the line switching section 52 includes two terminal arrays, one on each side. To one of these terminal arrays are connected the plurality of signal lines 20B corresponding to the first aperture as described above and the plurality of signal lines 22B corresponding to the second aperture as described above are connected, while a plurality of signal lines 48A connected to a CW transmission section 48 and a plurality of signal lines 50A connected to a CW reception section 50 are connected to the other terminal array.

In this embodiment, the line switching section 52 connects the plurality of signal lines 48A to the plurality of signal lines 20B when the first transmitting and receiving aperture pattern is selected, as indicated by lines A in FIG. 1. Thus, the plurality of transducer elements included in the first aperture 20 are connected to the CW transmission section 48. Consequently, the first aperture 20 functions as a transmitting aperture. Further, when the first transmitting and receiving aperture pattern is selected, the plurality of signal lines 22B are connected to the plurality of signal lines 50A, whereby the plurality of transducer elements included within the second aperture 22 are connected to the CW reception section 50. Thus, the second aperture 22 functions as a receiving aperture.

When, on the other hand, the second transmitting and receiving aperture pattern is selected, the line switching section 52 connects the plurality of signal lines 48A to the plurality of signal lines 22B (as indicated by lines B in FIG. 1). Simultaneously, the line switching section 52 connects the plurality of signal lines 20B to the plurality of signal lines 50A. With this connection, the second aperture 22 functions as a transmitting aperture. More specifically, the plurality of transducer elements included in the second aperture 22 are connected to the CW transmission section 48. At the same time, the first aperture 20 functions as a receiving aperture, by connecting the plurality of transducer elements included within the first aperture 20 to the CW reception section 50.

The control section 58, which will be described below, switches from the first transmitting and receiving aperture pattern to the second transmitting and receiving aperture pattern, and then from the second transmitting and receiving aperture pattern to the first transmitting and receiving aperture pattern in accordance with predetermined time conditions. Subsequently, such a pattern change will be repeated. As such, the transmitting aperture and the receiving aperture are interchanged at predetermined time intervals.

The CW transmission section 48 generates a transmitting signal (a continuous signal), and the CW reception section 50 performs a phase alignment and summation process with respect to a plurality of receiving signals (continuous signals). In this case, a phase detector method or the like is used. After being output from the CW reception section 50, the receiving signals subjected to the above-described process are input to an FFT (fast Fourier transformer) 52 serving as a frequency analyzer. The FFT 52 performs frequency analysis with respect to the receiving signals (Doppler components). The spectrum data at each time point obtained as a result of the frequency analysis is output to a waveform processing section 54 which is a module for forming a Doppler waveform. In the present embodiment, the waveform processing section 54 is also provided with a function of automatically tracing the Doppler waveform. The waveform processing section 54 also has an interpolating function on the time axis, and processes a missing portion which is generated in a waveform or a line on the time axis by the interpolating process. This process will be described below with reference to FIG. 3. The data of Doppler waveform which is generated in the waveform processing section 54 is output to the display processing section 46.

The display section 56 displays a B mode image, a Doppler waveform, and other images. In general, when observing blood flow within a living body, the B mode is first selected and a B mode image is displayed on the screen. A user then designates a target position on the B mode image where they wishes to observe the blood flow. Then, CW Doppler mode is selected, and a transmission and reception condition is automatically set such that the transmitting beam and the receiving beam cross each other at this target position. Doppler information from a sample volume around the target position is obtained and is displayed as a Doppler waveform on the time axis. In such a case, when a predetermined event occurs, such as when a predetermined time has elapsed or when a new measuring target is set, for example, a pattern change as described above is performed. More specifically, the positions of the transmitting aperture and the receiving aperture are interchanged. This process is then repeated.

The control section 58 controls the operation of each structure shown in FIG. 1. In particular, the control section 58 performs transmission and reception control including changing the transmitting and receiving aperture pattern as described above in the CW Doppler mode. An operation panel 60 includes a keyboard, a track ball, and so on. The input information which is set in the operation panel 60 is output to the control section 58.

According to the ultrasound diagnostic apparatus shown in FIG. 1, it is possible to change the transmitting and receiving aperture pattern in accordance with a predetermined condition to thereby shift the position of the transmitting aperture with time in continuous wave Doppler mode. This structure allows heat generating portions to be dispersed on the array transducer and can solve the problem of uneven, advanced deterioration of a specific transducer element. Although in the related art it is necessary to decrease the acoustic power due to localized heat generation, according to the present embodiment, with dispersion of heat generating portions, it is possible to prevent a situation of such a power limitation as much as possible, thereby efficiently solving the problem of reduced sensitivity which results when the present invention is not employed.

Figure 2:
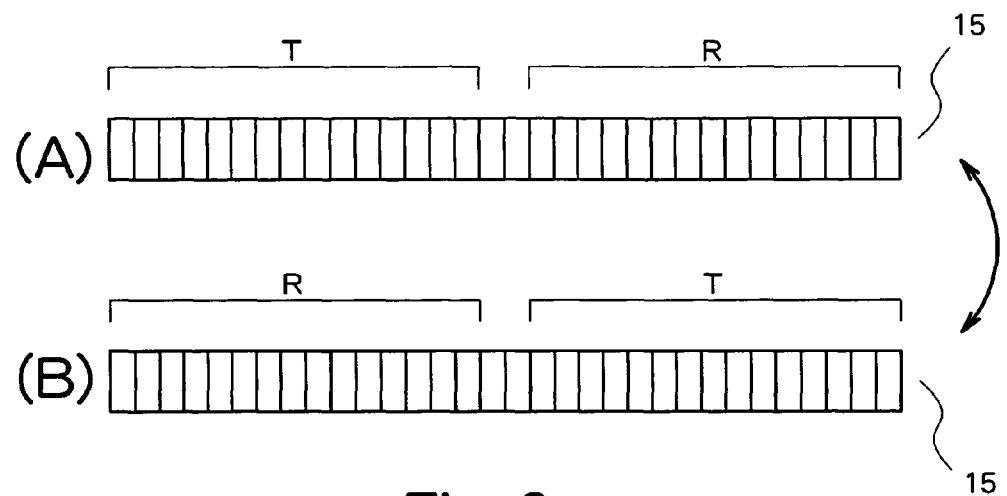
FIG. 2 shows a first transmitting and receiving aperture pattern and a second transmitting and receiving aperture pattern of the embodiment.

Referring to FIG. 2, view (A) shows the first transmitting and receiving aperture pattern and view (B) shows the second transmitting and receiving aperture pattern. As shown, the transmitting aperture T and the receiving aperture R are interchanged at a predetermined interval. Here, it is desirable that a gap region be provided as necessary, with the number of transducer elements forming the gap region not being limited by the present invention. It is also possible to alternately arrange the transducer elements for transmission and the transducer elements for reception from one end of the array transducer to the other, to thereby simultaneously form a transmitting aperture and a receiving aperture having the size of the overall array transducer. However, in order to reduce acoustic crosstalk, it is desirable to adopt the pattern shown in FIG. 2, in which each of the transmitting aperture and the receiving aperture is formed in a block shape.

Figure 3:
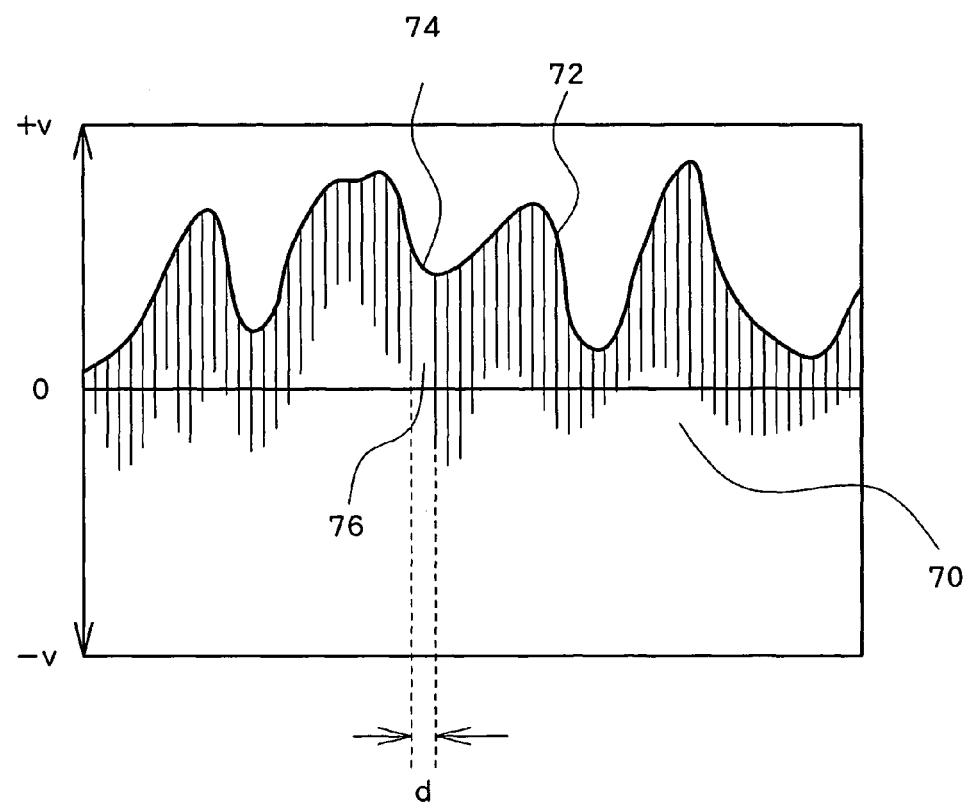
FIG. 3 is a diagram showing an example Doppler waveform.

FIG. 3 shows one example of a Doppler waveform formed by the waveform processing section 54. In FIG. 3, the horizontal axis is a time axis, and the vertical axis indicates the Doppler shift frequency, i.e. the blood flow rate. The brightness of each pixel represents power. As is known, the Doppler waveform is formed as a set of a plurality of spectrums arranged along the time axis. Each spectrum is formed by a plurality of pixels (represented by one line in FIG. 3) arranged in the vertical direction. In the course of continuous wave Doppler mode being performed continuously, a pattern change is performed at predetermined time intervals, as a result of which a missing portion 76 is generated on the Doppler waveform 72. Such a missing portion 76 is generated in a small period d. In order to eliminate this missing portion 76, the interpolating process described above is performed on the Doppler waveform. Further, when the trace line 72 is drawn by performing an auto trace process with respect to the Doppler waveform 72, the interpolating process is applied during the small period d. Specifically, two line fragments existing on both sides of the small period d are connected (see numeral 74) to form one trace line 72. On the other hand, when a display mode in which the Doppler waveform extends in the direction of the time axis and is refreshed at fixed intervals is selected, by synchronizing the display refresh timing with the pattern change timing, the missing portion is not displayed on the screen. In other words, it is possible to ensure that the missing portion 76 appears during a period when the display is blank.

When it is necessary to correct the flow rate at the time of the pattern changing, the range of the vertical axis on the Doppler waveform or the base line level can be corrected. In the present embodiment, however, because the first aperture and the second aperture are set symmetrically with respect to the center of the array transducer, angle correction is not necessary, even when the transmitting aperture and the receiving aperture are switched, as will be described below with reference to FIG. 4. Here, the angle correction (rate correction) which is required due to a difference between the ultrasound beam direction and the blood flow direction should be performed as in the conventional ultrasound diagnostic apparatus. Such an angle correction can be performed under the same conditions, before and after the pattern change.

Whether or not it is necessary to perform the angle correction in a case where the transmitting aperture and the receiving aperture which are symmetrical with respect to each other are interchanged will be studied.

Figure 4:
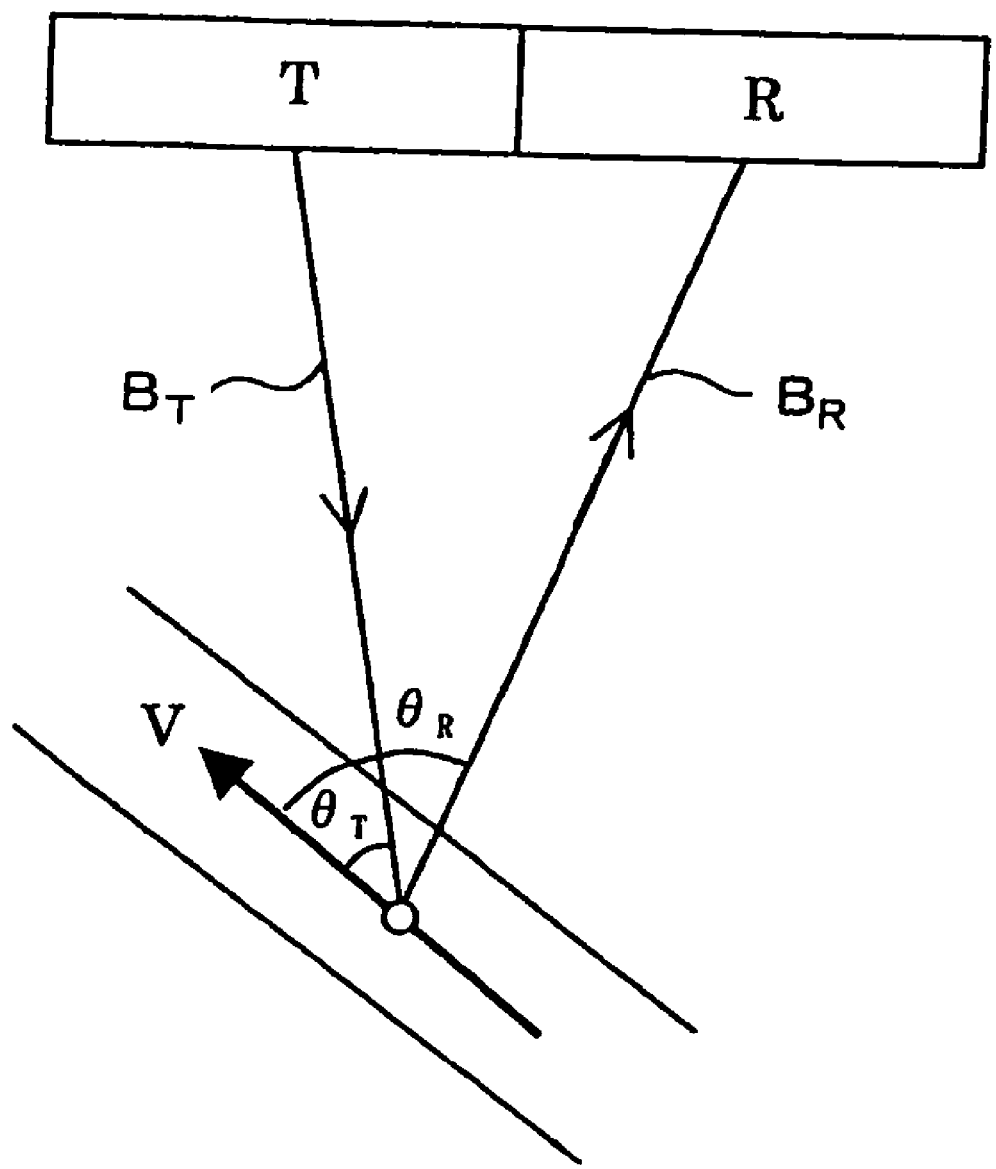
FIG. 4 is a view showing a relationship among a transmitting beam, a receiving beam, and a blood flow vector.

Referring to FIG. 4, the transmitting aperture is indicated by T and the receiving aperture is indicated by R. A blood flow within a blood vessel is indicated by a vector V. The angle which is formed between the transmitting beam $B_T$ and the vector V is $\theta_T$, and the angle which is formed by the receiving beam $B_R$ and the vector V is $\theta_R$. Assuming that the frequency of ultrasound is $f_0$ and the sound velocity within a living body is C, the frequency $f_1$ of a transmitting wave which is observed in the blood flow is represented by the following equation (1) and the frequency $f_2$ of a reflected wave (receiving wave) which is observed at the receiving aperture R is represented by the following equation (2):

$$f_1 = (1 + V \cdot \cos\theta_T / C) \cdot f_0 \quad (1)$$

$$f_2 = (1 - V \cdot \cos\theta_R / C)^{-1} \cdot f_1 \quad (2)$$

Here, when the equation (1) is substituted for the equation (2), the following equation (3) is obtained:

$$f_2 = ((1 + V \cdot \cos\theta_T / C) / (1 - V \cdot \cos\theta_R / C)) \cdot f_0 \quad (3)$$

By multiplying each of numerators and denominators in the right side in the above equation (3) with $(1 + V \cdot \cos\theta_R / C)$ and also considering that $(V/C)^2$ is substantially 0 because of $V/C \ll 1$, the above equation (3) can be rewritten as follows:

$$f_2 = f_0 + (V/C) \cdot (\cos \theta_T / \cos \theta_R) \cdot f_0 \quad (4)$$

Accordingly, the Doppler shift frequency $f_d$ is obtained as follows:

$$f_d = f_2 - f_1 = (V/C) \cdot (\cos \theta_T / \cos \theta_R) \cdot f_0 \quad (5)$$

Here, if $\theta_T + \theta_R = \theta$ is defined, the above equation (5) can be expressed in the following equation (6):

$$f_d = 2 \cdot V \cdot f_0 \cdot \cos \theta / C \quad (6)$$

The above equation (6) is a known equation for calculating a Doppler shift frequency. Here, $\theta_T + \theta_R = \theta$ is satisfied even if the transmitting beam and the receiving beam are exchanged and $f_d$ is therefore unchanged. In other words, even if a first transmitting and receiving aperture pattern and second transmitting and receiving aperture pattern which are in a symmetrical relationship with respect to each other are exchanged (i.e. even if the transmitting beam and the receiving beam are exchanged), the measured result remains the same. Accordingly, when switching is performed between two patterns each having a symmetrical relationship, angle correction is not necessary. However, when the above calculation cannot be satisfied due to various factors, it is desirable to perform angle correction. Here, the velocity correction (angle correction) in accordance with an angle formed by the blood flow vector and the ultrasound beam may be performed as necessary in a manner similar as in conventional ultrasound diagnostic apparatuses.

Figure 5:
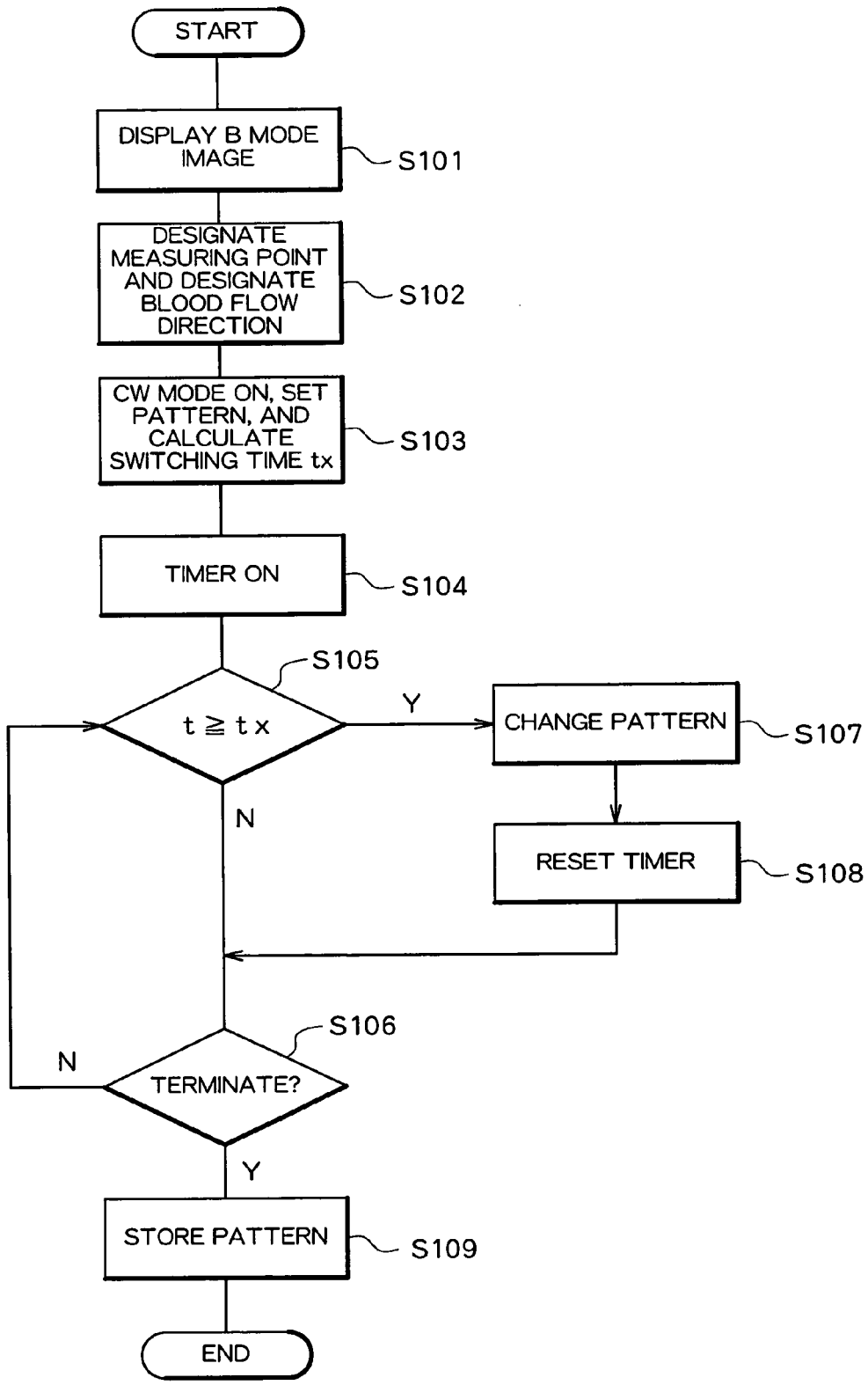
FIG. 5 is a flowchart for explaining an example operation of the ultrasound diagnostic apparatus shown in FIG. 1.

Referring to FIG. 5, an example of operation of the apparatus shown in FIG. 1 will be described. First, the B mode is selected in step S101, and a B mode image is displayed as a two-dimensional monochrome tomographic image on the screen. On this screen, a user designates a measuring point functioning as a measuring target by coordinate adjustment of the position marker. Further, the user can input the direction of a blood flow by aligning the arrow extending from the measuring point with the blood flow direction. This information is used as information for angle correction.

In step S103, control of continuous wave Doppler mode is started. At this time, a transmitting and receiving aperture pattern is selected, and also a switching time tx which will be described below is calculated. Here, at the time of pattern selection, it is possible to refer to the transmitting and receiving aperture pattern which was used the last during the immediately preceding measuring operation and select a transmitting and receiving aperture pattern which is different from the last transmitting and receiving aperture pattern. In this case, the time period in which the transmitting and receiving aperture pattern has been used during the immediately preceding measuring operation may be considered. For example, a transmitting and receiving aperture pattern which is different from that used in the immediately preceding measuring operation may be selected for the next measuring operation only when a certain transmitting and receiving aperture pattern has been used longer than a predetermined time period. The switching time tx is set in accordance with the transmission condition or the like. For example, the switching time tx is calculated by referring to parameters resulting from the temperature increase, such as a transmitting voltage, a transmitting power, a depth of a focus point, and so on. As the switching time tx, several tens of seconds to several minutes is set. Of course, the switching time tx may be set to a fixed value thereby eliminating the need for these calculations, or the switching time tx may be set freely by the user. Further, the switching time tx can be matched to the display refresh rate.

At step S104, a timer is actuated, and transmission and reception of a continuous wave is started. At step S105, it is determined whether or not the time t which is measured by the timer reaches the switching time tx. If the time t does not reach the switching time tx, it is then determined at step S106 whether or not the current measuring operation is caused to terminate. If it is determined that the current measuring operation is not caused to terminate, the process in step S105 is repeated.

If the time t has reached the switching time tx in step S105, then the process proceeds to step S107 in which a pattern change is performed. More specifically, a pattern change from the transmitting and receiving aperture pattern which is currently being used to another transmitting and receiving aperture pattern is performed. As a result of this pattern change, the transmitting aperture shifts to a different position to thereby shift the heat generating portion to another location. Consequently, further temperature increase is suppressed, or the temperature is reduced, around the transmitting aperture used during the previous transmission and reception operation. On the other hand, while heat is generated at the position of the transmitting aperture which is newly set for the next measuring operation, it is possible to use time control or event management to prevent continuous heat generation over a long time period. At step S108, the timer is reset upon the pattern change, so that measurement using the timer concerning the new transmitting and receiving aperture pattern is resumed.

If termination of the current measuring operation is determined at step S106, an identifier of the transmitting and receiving aperture pattern which is currently being used (and the elapsed time, if necessary) is registered on the memory. This information can be referred to in the next measuring operation, if necessary.

Accordingly, with the operation example shown in FIG. 5, it is possible to change the transmitting and receiving aperture pattern as necessary, each time the continuous wave Doppler mode is designated or each time the measuring portion is changed. Consequently, even when a short-time measuring operation is performed repeatedly, for example, the transmitting and receiving aperture pattern is changed for each operation, so that degradation of the transducer elements can be equalized over the whole array transducer. Further when one transmitting and receiving aperture pattern is continuously employed, this transmitting and receiving aperture pattern is forcibly reset to another pattern after a predetermined time has elapsed, to thereby effectively prevent the problem of excessive increase of the temperature of one portion on the array transducer from occurring.

Figure 6:
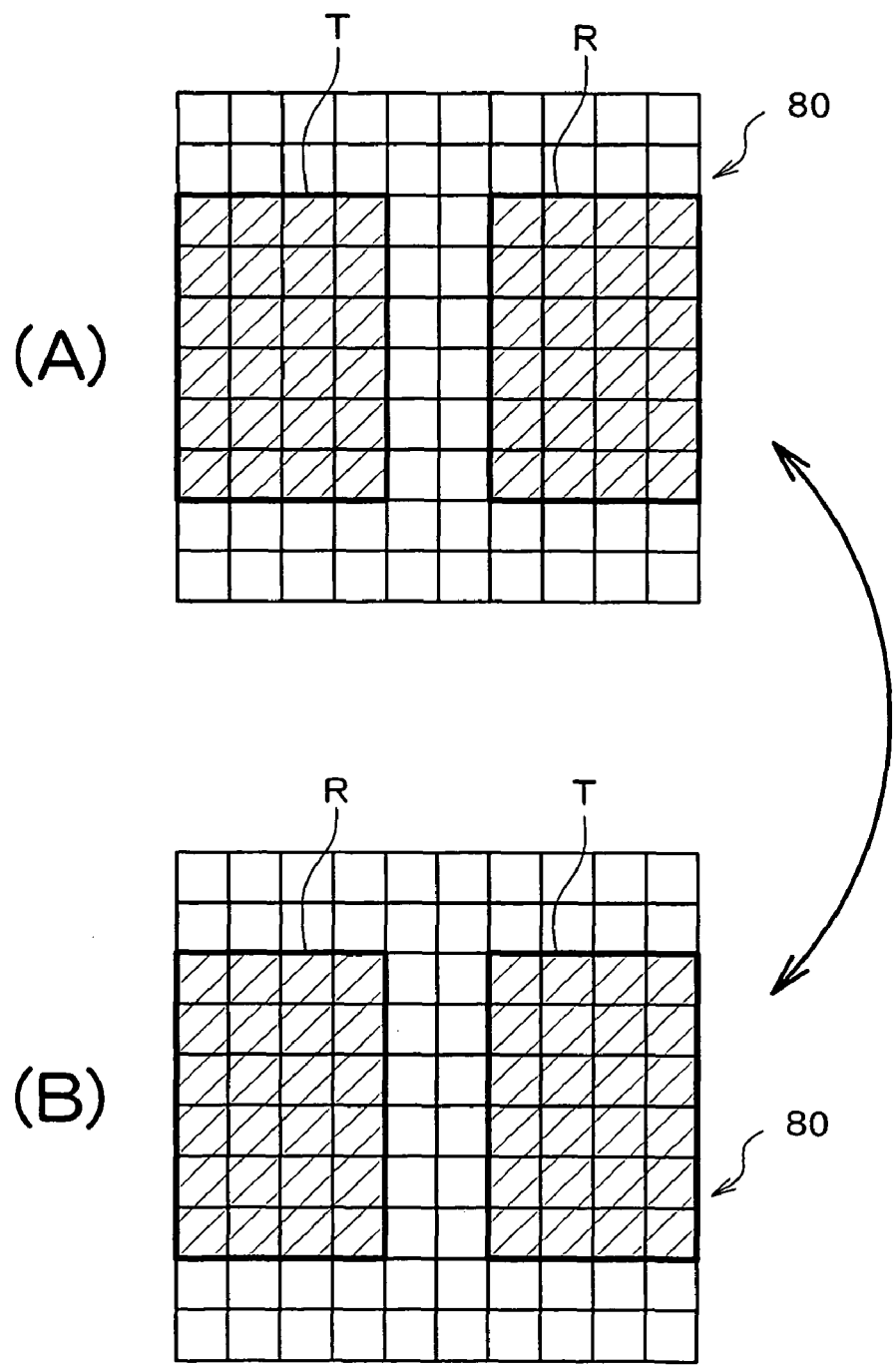
FIG. 6 explains a change of the transmitting and receiving aperture pattern on a 2D transducer array.

FIG. 6 shows a 2D array transducer 80. View (A) shows a first transmitting and receiving aperture pattern and view (B) shows a second transmitting and receiving aperture pattern. These aperture patterns are in a symmetrical relationship. Even when these patterns are switched to thereby change the positions of the transmitting aperture T and the receiving aperture R, no angle correction resulting from such a change is necessary. A variety of two-dimensional transmitting and receiving aperture patterns may be considered.

Figure 7:
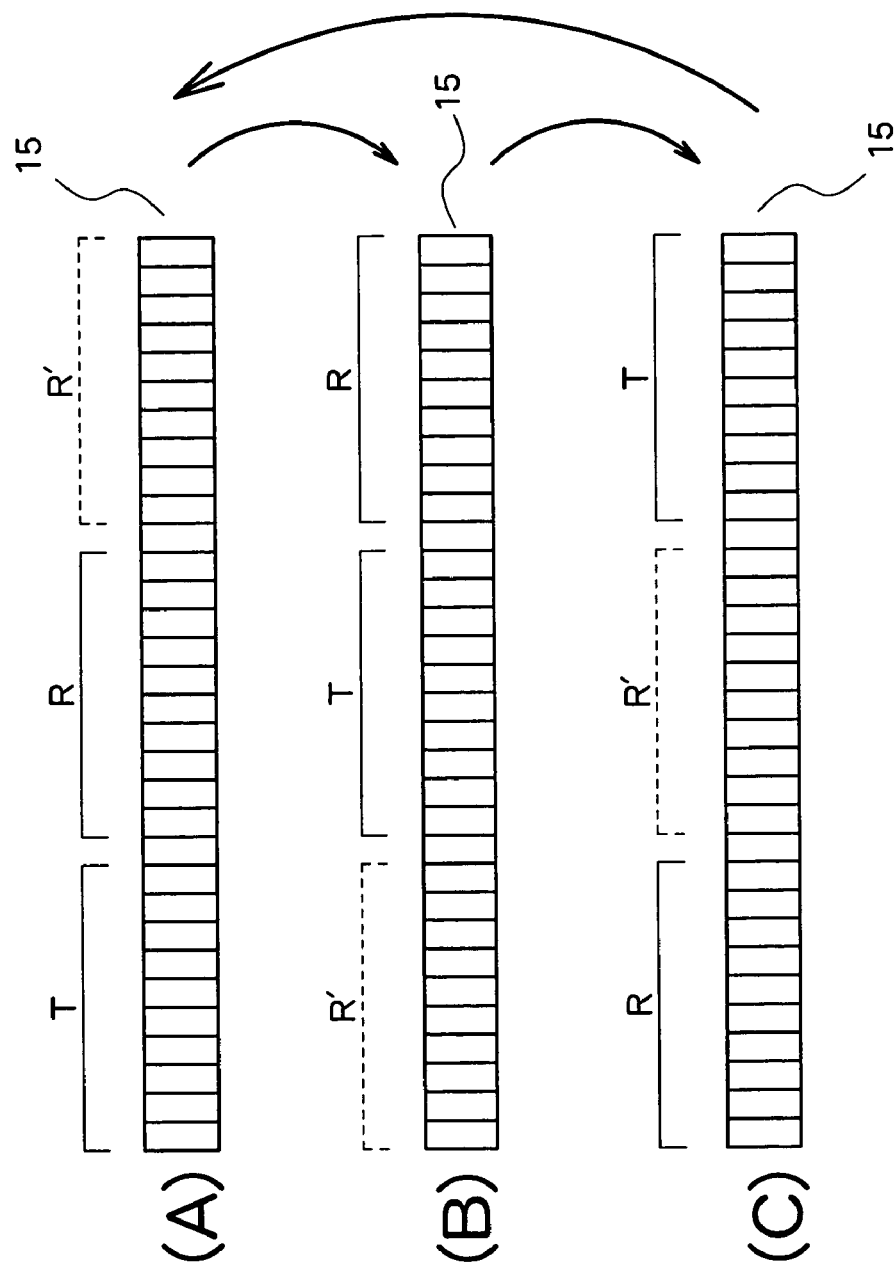
FIG. 7 shows a change among three transmitting and receiving aperture patterns.

FIG. 7 shows a 1D array transducer 15. View (A) shows a first transmitting and receiving aperture pattern, view (B) shows a second transmitting and receiving aperture pattern, and view (C) shows a third transmitting and receiving aperture pattern. These transmitting and receiving aperture patterns are used in rotation. In FIG. 7, T represents a transmitting aperture, R represents a receiving aperture, and R' represents a receiving aperture which is additionally set when necessary. As shown in views (A) to (C), by shifting the transmitting aperture T in rotation, uniform heat generation and uniform wear can be achieved over the entire region of the array transducer. Here, when the structure shown in FIG. 7 is adopted, because the setting conditions of the transmitting beam and the receiving beam are changed when the pattern is changed, it is desirable to perform flow rate correction, gain correction, and so on, as required, at the time of the pattern change.

Further, the line switching section 52 shown in FIG. 1 is a circuit for switching between the first aperture 20 and the second aperture 22 as transmitting and receiving apertures, respectively. Here, a switching matrix, when provided as the line switching section 52, can cope with more various pattern changes.

Figure 8:
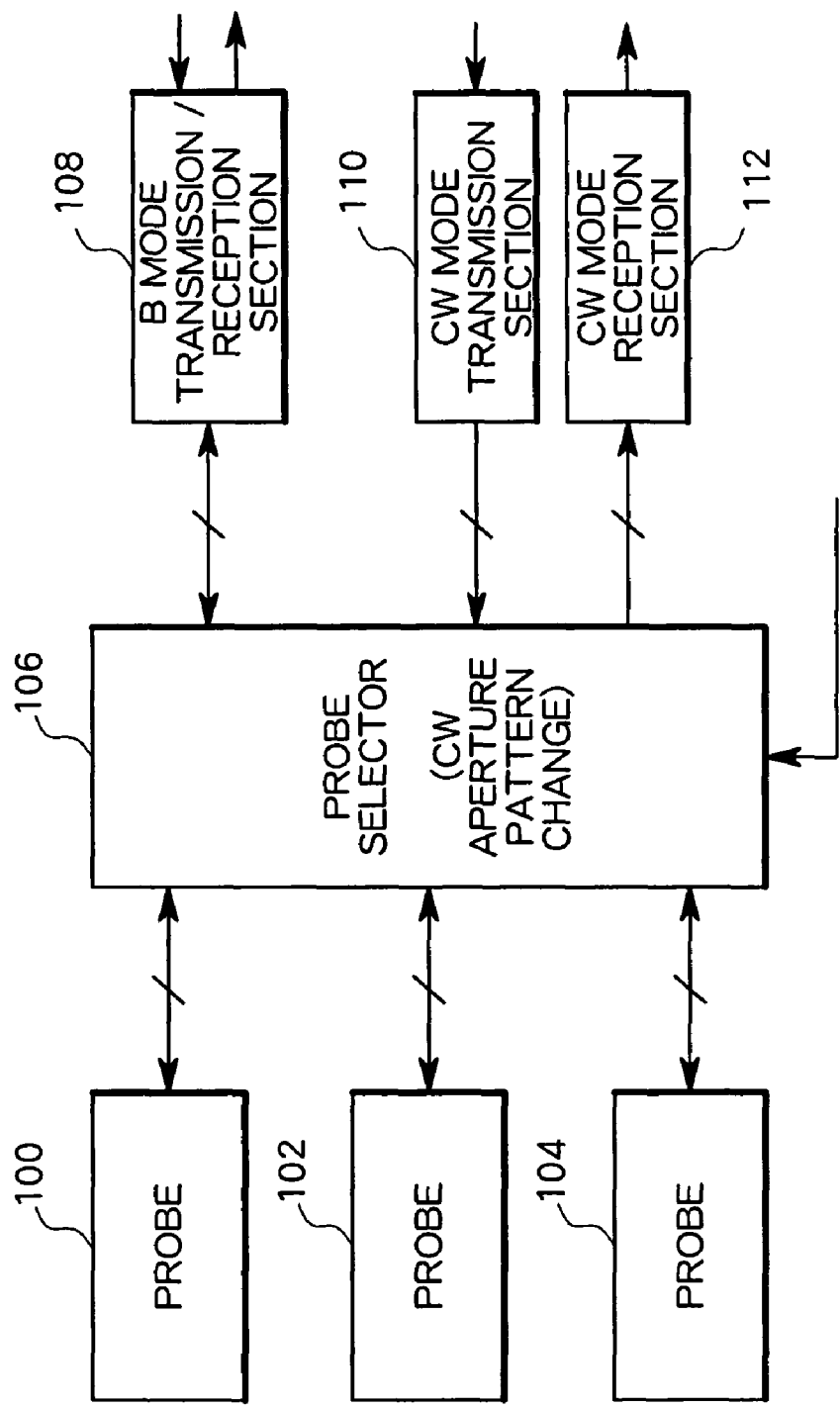
FIG. 8 is a block diagram of an ultrasound diagnostic apparatus having a probe selector for changing among a plurality of probes according to another embodiment of the present invention.
Figure 9:
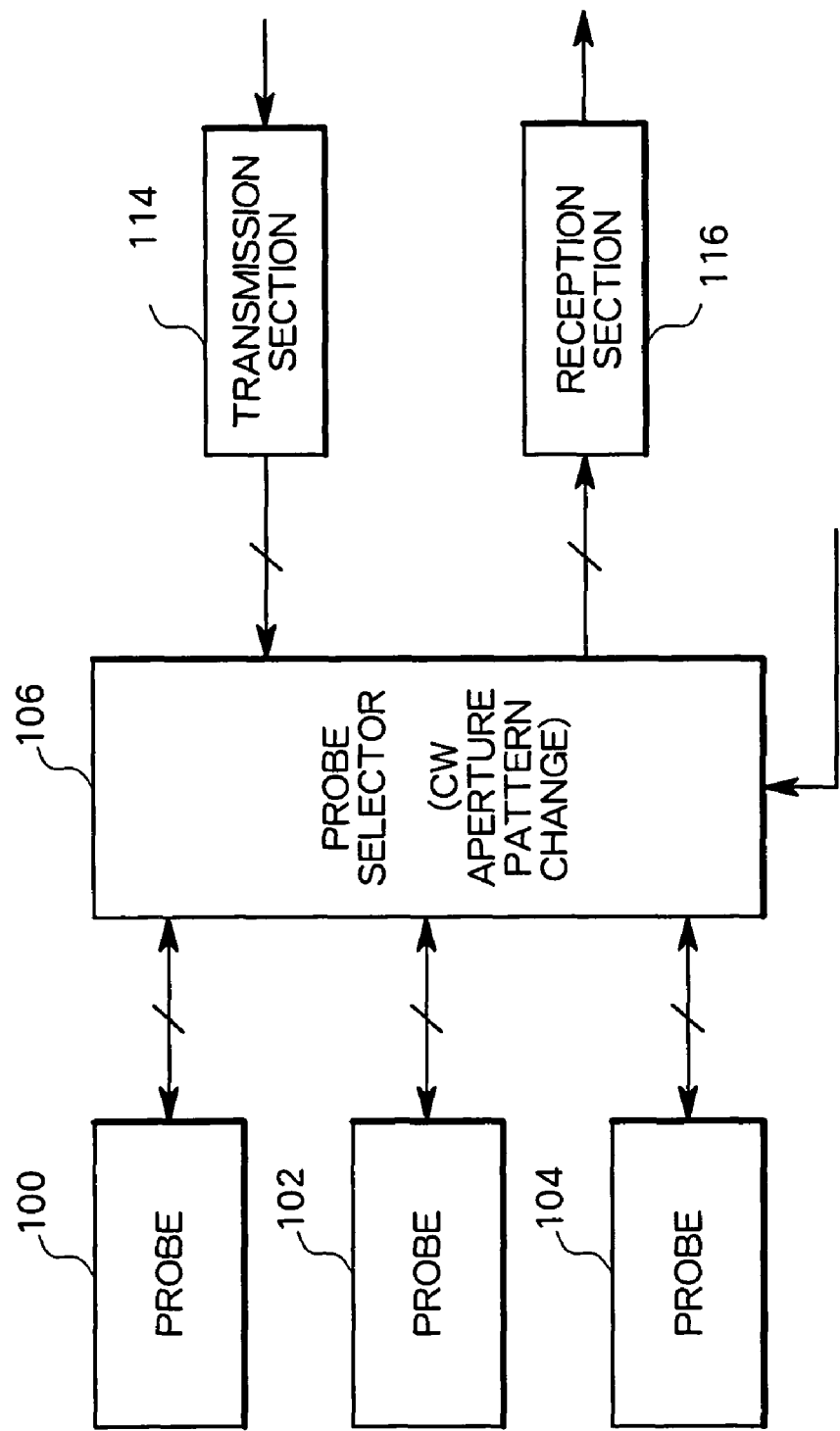
FIG. 9 is a block diagram of an ultrasound diagnostic apparatus having a probe selector for changing among a plurality of probes according to still another embodiment of the present invention.

FIGS. 8 and 9 show other structure examples. In FIG. 8, a probe selector 106 is provided within the apparatus body of an ultrasound diagnostic apparatus. Although plurality of probes 100, 102, and 104 are simultaneously connected to the probe selector 106, only a designated probe is actually used at one time. Further, a B mode transmission/reception section 108 (corresponding to the transmission/reception section 40 of FIG. 1), a CW mode transmission section 110 (corresponding to the CW transmission section 48 of FIG. 1), and a CW mode reception section 112 (corresponding to the CW reception section 50 of FIG. 1) are connected to the probe selector 106. The probe selector 106 is formed as a line switching module such as a multiplexer and a switching matrix. The probe selector 106, in B mode, connects the B mode transmission/reception section 108 and the specific probe which is selected with each other. Further, the probe selector 106, in CW mode, connects the specific probe which is selected to the CW mode transmission section 110 and the CW mode reception section 112. Also, the probe selector 106, in CW mode, has a function of changing the transmitting and receiving aperture pattern (corresponding to the function of the line switching section 52 in FIG. 1) at a predetermined timing. For example, the positions of the CW transmitting aperture and the CW receiving aperture are switched at a predetermined timing. In other words, the positions of the CW transmitting aperture are changed in rotation. Thus, it is possible to solve the problem that only a specific portion on the array transducer is heated or deteriorated. The operation of the probe selector 16 is controlled by a controller which is not shown.

FIG. 9 shows an example structure which differs from the example structure shown in FIG. 8. In FIG. 9, elements similar to those in FIG. 8 are designated by the same numerals and will not be described again. Referring to FIG. 9, a transmission section 114 is a common transmission section which functions in both B mode and CW mode. Similarly, a reception section 116 is a common reception section which functions in both B mode and CW mode. In the structure shown in FIG. 9, as in the structure shown in FIG. 8, the probe selector 106 has a function of changing the transmitting and receiving aperture pattern at a predetermined timing. Thus, it is possible to solve the problem that only a specific portion on the array transducer is heated or deteriorated.

With the structures shown in FIGS. 8 and 9, a change of the transmitting and receiving aperture pattern (i.e. rotation of the transmitting aperture) can be performed using the probe selector 106, thereby eliminating the need for providing a separate line switching section. However, it is also possible to provide a line switching section within a connector or within a probe head in the probe which is used in CW mode while the probe selector 106 is used in a manner similar as in a conventional apparatus.

While the preferred embodiments of the present invention have been described using specific terms, such description is for illustrative purposes only, and it is to be understood that changes and variations may be made without departing from the spirit or scope of the appended claims.

What is claimed is:

1. An ultrasound diagnostic apparatus, comprising:
an array transducer including a plurality of transducer elements;
a transmission/reception section for B mode coupled to the array transducer;
a plurality of signal lines provided between the array transducer and the transmission/reception section for B mode, the plurality of signal lines having a plurality of branch points;
a plurality of branch lines extending from said plurality of branch points;
a transmission section for a continuous wave Doppler mode configured to supply a plurality of continuous transmitting signals to a plurality of transducer elements forming transmitting aperture patterns which are set on the array transducer in the continuous wave Doppler mode;
a reception section for the continuous wave Doppler mode configured to process a plurality of continuous receiving signals supplied from a plurality of transducer elements forming receiving aperture patterns which are set on the array transducer in the continuous wave Doppler mode;
a control section configured to produce a control signal to sequentially change transmitting and receiving aperture patterns set on the array transducer to thereby sequentially change a position of the transmitting aperture which is set on the array transducer in the continuous wave Doppler mode;
a line switching section provided between the plurality of branch lines and the transmission and reception sections for the continuous wave Doppler mode;
the control section further configured to control the line switching section to sequentially change the transmitting and receiving aperture patterns set on the array transducer while transmission and reception of a continuous wave is being performed with respect to a specific measuring target to thereby sequentially change a position of the transmitting aperture patterns which are set on the array transducer during the continuous wave Doppler mode;
image forming means configured to form a waveform image based upon a receiving signal having been processed which is output from the reception section; and
a display section for displaying said waveform image;
wherein:
the transmitting and receiving apertures are simultaneously changed on the array transducer in the continuous wave Doppler mode;
the transmitting aperture before the change of the transmitting and receiving aperture patterns and the transmitting aperture after the change of the transmitting and receiving aperture patterns do not overlap each other in the continuous wave Doppler mode; and
the control section is further configured to synchronize a timing of the changes of the transmitting and receiving aperture patterns with a refresh timing of the waveform image so as to prevent an effect caused by the change of the transmitting and receiving aperture patterns from appearing on the display section for displaying the waveform image.

2. An apparatus according to claim 1, wherein
the control section is configured to selectively set the transmitting and receiving aperture patterns among a plurality of transmitting and receiving aperture patterns including a first transmitting and receiving aperture pattern and a second transmitting and receiving aperture pattern set on the array transducer, the first transmitting and receiving aperture pattern has a first transmitting aperture set on one side of the array transducer and a first receiving aperture set on the other side of the array transducer, and the second transmitting and receiving aperture pattern has a second receiving aperture set on the one side of the array transducer and a second transmitting aperture set on the other side of the array transducer.

3. An apparatus according to claim 2, wherein the first transmitting and receiving aperture pattern has a symmetrical shape with respect to a center of the array transducer, and the second transmitting and receiving aperture pattern has a symmetrical shape with respect to a center of the array transducer.

4. An apparatus according to claim 2, wherein the first transmitting aperture of the first transmitting and receiving aperture pattern and the second receiving aperture of the second transmitting and receiving aperture pattern are set at the same position on the array transducer, and the first receiving aperture of the first transmitting and receiving aperture pattern and the second transmitting aperture of the second transmitting and receiving aperture pattern are set at the same position on the array transducer.

5. An apparatus according to claim 2, wherein the first transmitting and receiving aperture pattern further includes a first gap region which is set between the first transmitting aperture and the first receiving aperture, and the second transmitting and receiving aperture pattern further includes a second gap region which is set between the second transmitting aperture and the second receiving aperture.

6. An apparatus according to claim 2, wherein the control section is configured to alternately select the first transmitting and receiving aperture pattern and the second transmitting and receiving aperture pattern.

7. An apparatus according to claim 1, wherein the ultrasound diagnostic apparatus includes an ultrasound probe having the array transducer and an apparatus body to which the ultrasound probe is connected, and the line switching section is provided in the ultrasound probe.

8. An apparatus according to claim 1, wherein the ultrasound diagnostic apparatus includes an ultrasound probe having the array transducer and an apparatus body to which the ultrasound probe is connected, and the line switching section is provided in the apparatus body.

9. An apparatus according to claim 1, wherein the transmission section for the continuous wave Doppler mode is used exclusively in connection with the continuous wave Doppler mode, the reception section for the continuous wave Doppler mode is used exclusively in connection with the continuous wave Doppler mode;

the line switching section is configured to:

selectively connect a plurality of signal lines connected to a plurality of transducer elements within a first region of the array transducer to the transmission section or the reception section, and selectively connect a plurality of signal lines connected to a plurality of transducer elements within a second region of the array transducer to the transmission section or the reception section; and the control section, when the first transmitting and receiving aperture pattern is selected, is configured to connect the plurality of signal lines connected to the plurality of transducer elements within the first region to the transmission section and is further configured to connect the plurality of signal lines connected to the plurality of transducer elements within the second region to the reception section, and, when the second transmitting and receiving aperture pattern is selected, is configured to connect the plurality of signal lines connected to the plurality of transducer elements within the first region to the reception section and is further configured to connect the plurality of signal lines connected to the plurality of transducer elements within the second region to the transmission section.

* * * * *